US007947310B2

(12) United States Patent
Rind

(10) Patent No.: US 7,947,310 B2
(45) Date of Patent: May 24, 2011

(54) METHOD OF TREATING STROKE OR BRAIN INJURY PATIENTS BASED ON THE INTRAVENOUS ADMINISTRATION OF MAGNESIUM CATIONS AND CONCURRENT ADMINISTRATION OF AN OXYGEN GAS MIXTURE

(75) Inventor: Bruce Rind, Derwood, MD (US)

(73) Assignee: Relox Medical, LLC, Fort Lauderdale, FL (US)

(*) Notice: Subject to any disclaimer, the term of this patent is extended or adjusted under 35 U.S.C. 154(b) by 1162 days.

(21) Appl. No.: 11/397,428

(22) Filed: Apr. 4, 2006

(65) Prior Publication Data
US 2006/0280807 A1 Dec. 14, 2006

Related U.S. Application Data

(60) Provisional application No. 60/668,219, filed on Apr. 5, 2005.

(51) Int. Cl.
*A61K 31/14* (2006.01)
*A61K 33/00* (2006.01)
*A61K 47/00* (2006.01)

(52) U.S. Cl. ......... 424/681; 424/600; 424/613; 514/771

(58) Field of Classification Search .................. 424/600, 424/613, 681; 514/771
See application file for complete search history.

(56) References Cited

U.S. PATENT DOCUMENTS

| 4,933,178 | A | * | 6/1990 | Capelli | 424/403 |
| 5,533,981 | A | | 7/1996 | Mandro et al. | |
| 6,123,925 | A | * | 9/2000 | Barry et al. | 424/49 |
| 2008/0132844 | A1 | | 6/2008 | Peterson et al. | |
| 2008/0287873 | A1 | | 11/2008 | Liberatore et al. | |
| 2008/0306444 | A1 | | 12/2008 | Brister et al. | |

FOREIGN PATENT DOCUMENTS

WO 96/11024 4/1996

OTHER PUBLICATIONS

Merck Manual Online Medical Library article, entitled, "Cerebral Palsy"—accessed on Jan. 23, 2010 at www.merck.com/mmhe/print/sec23/ch284/ch284a.html.*
Pryde, P.G. and Mittendorf, R., "Contemporary Usage of Obstetric Magnesium Sulfate," Obstetrics & Gynecology, Sep. 2009, 114(3), pp. 669-673.*
Cahill, A.G. and Caughey, A.B. "Magnesium for neuroprophylaxis: fact of fiction?," American Journal of Obstetrics & Gynecology, Jun. 2009, 200(6), pp. 590-594.*
iSOC® Technology Oxygen Material Safety Data Sheet—accessed Jan. 24, 2010 at www.isocinfo.com/DocumentRoot/13/Oxygen.pdf.*
Bacterial Infections, Merck Manual Medical Home Edition, accessed May 10, 2010 at www.merck.com/mmhe/print/sec17/ch190/ch190a.html.*
"Herpes Simplex Virus Infections," Merck Manual Medical Home Edition, accessed May 10, 2010 at www.merck.com/mmhe/print/sec17/ch198/ch198e.html.*
"Ringworm (Tinea)," Merck Manual Medical Home Edition, accessed May 10, 2010 at www.merck.com/mmhe/print/sec18/ch212/ch212c.html.*
"Infections: Parasitic Infections," Merck Manual Medical Home Edition, accessed May 10, 2010 at www.merck.com/mmhe/print/sec17/ch196/ch196a.html.*
Kuby, J. Immunology, 3rd edition, W. H. Freeman and Company: New York, 1997, pp. 67, 365-378.*
Zuzan, O. and Muller-Vahl, H., "Die notarztliche Versorgung von Patienten mit vermutetem Schlanganfall: Analyse von 298 Fallen," Intensivmed. 1997, vol. 34, pp. 131-139 (Full article, includes an English Language Abstract).*
Gaby, A., "Intravenous Nutrient Therapy: the Myers Cocktail" Alternative Med. Review 7:389, 2002.
Muir, K. W., et al., A Randomized, Double-Blind, Placebo-Controlled Pilot Trial of Intravenous Magnesium Sulfate in Acute Stroke, Stroke, published online stroke.ahajournals.org/cgi/content/full/26/7/1183 1995 26:1183-1188. American Heart Association, Dallas.
Witmeier, A. et al., W.I.L.P.S Wireless Interfacing Linear Positioning Syringe, Team ECE 402 Senior Design Project—www.studiosapuri.com/writingEE402DfinalDesignReview.pdf, Oct. 23, 2002, Purdue University, Indiana.
Lampl, Y., et al., Intravenous Administration of Magnesium Sulfate in Acute Stroke: A Randomized Double-Blind Study, Clinical Neuropharmacology, 2001 24(1):11-15 Lippincott Williams & Wilkens, Inc., Philadelphia.
Muir, K. W., et al., Magnesium for acute stroke (Intravenous Magnesium Efficacy in Stroke trial): randomised controlled trial, The Lancet, Feb. 7, 2004 363(9407):439-445.
Muir, K.W. et al., New experimental and clinical data on the efficacy of pharmacological magnesium infusions in cerebral infarcts, Magnesium Research, 1998 11(1):43-56, John Libbey Eurotext Limited, Le Pecq, France.
Rusyniak, D. E., et al., Hyperbaric Oxygen Therapy in Acute Ischemic Stroke: Results of the Hyperbaric Oxygen in Acute Ischemic Stroke Trial Pilot Study, Stroke, published online Jan. 16, 2003, 34:571-574, American Heart Association, Dallas.
Saver, J. L., et al., Prehospital Neuroprotective Therapy for Acute Stroke: Results of the Field Administration of Stroke Therapy-Magnesium (FAST-MAG) Pilot Trial, Stroke, published online Mar. 11, 2004, 35:e106-e108, American Heart Association, Dallas.
Schouten, J. W., Neuroprotection in traumatic brain injury: a complex struggle against the biology of nature, Current Opinion in Critical Care 2007 13:134-142, Lippincott Williams & Wilkins, Philadelphia.
Temkin, N. R., et al., Magnesium sulfate for neuroprotection after traumatic brain injury: a randomised controlled trial, The Lancet Neurology, published online Nov. 30, 2006, 6(1):29-38.
International PCT Search Report and the Written Opinion of the International Searching Authority, or the Declaration, PCT/US2010/040893, 10 pages.
Vink, Robert et al., Magnesium in acute and chronic brain injury: an update, Magnesium Research. vol. 22, No. 3, 158-62, Sep. 2009, 12th International Magnesium Symposium.
U.S. Appl. No. 12/498,500, Office Action mailed Dec. 13, 2010, 23 pgs.

* cited by examiner

*Primary Examiner* — James H Alstrum Acevedo
(74) *Attorney, Agent, or Firm* — Fredrikson & Byron, P.A.

(57) ABSTRACT

A method for treating a patient comprising: (a) injecting into the bloodstream of a patient is breathing a gas mixture having greater than 25% oxygen an aqueous solution comprising: 0.1 to 0.8 M Mg++ and having an osmolarlity less than about 1500 mOSm/l; and (b) increasing the rate of injection at least until the patient feels a sensation of warmth is described.

30 Claims, No Drawings

METHOD OF TREATING STROKE OR BRAIN INJURY PATIENTS BASED ON THE INTRAVENOUS ADMINISTRATION OF MAGNESIUM CATIONS AND CONCURRENT ADMINISTRATION OF AN OXYGEN GAS MIXTURE

RELATED APPLICATION INFORMATION

This application claims priority to U.S. provisional application Ser. No. 60/668,219, filed on Apr. 5, 2005, which is hereby incorporated by reference.

BACKGROUND OF THE INVENTION

Intravenous vitamin and mineral formulations have be used for the treatment of certain clinical conditions. The so-called "Myers' Cocktail", which contain magnesium, calcium, B vitamins and vitamin C is an example of such a formulation (Gaby 2002 Alternative Medicine Review 7:389).

SUMMARY OF THE INVENTION

The invention features a method for treating disorders such as stroke, cerebral palsy and brain/head trauma and other injuries. In addition, the method is useful for treating patients after surgery to speed healing and recovery by administering a solution containing certain ions and nutrients to a patient, preferably while the patient is breathing pure or nearly pure oxygen or a mixture of gases having greater than 21% oxygen. The methods of the invention can also be used to promote healing of damaged tissue, for example, damaged muscle tissue. The method is useful for tissue damage caused by any of a wide variety of factors, including, bruising, ischemia-reperfusion injury, infection, and inflammation.

Described herein is a method for treating a patient comprising: (a) injecting into the bloodstream of a patient is breathing a gas mixture having greater than 25% oxygen an aqueous solution comprising: 0.1 to 0.8 M Mg++ and having an osmolarlity less than about 1500 mOSm/l; and (b) increasing the rate of injection at least until the patient feels a sensation of warmth. In some embodiments, the method entails treating a region of the body of a patient and increasing the rate of injection at least until the patient feels a sensation of warmth in the region of the body to be treated. In some embodiments the patient provides feedback regarding the sensation of warmth so that a sensation of warmth in the target area can be achieved and/or maintained for a desired period of time. In some embodiments are temperature measuring device (e.g., a infrared temperature measuring device) is used to monitor increase in warmth of a target area of the patient's body. In some embodiments the rate of administration of the solution is varied based on feedback from the patient and/or measurements made by the temperature measurement device.

In various embodiments: the patient is administered a breathing mixture comprising at least 40% oxygen; the patient is administered a breathing mixture comprising at least 60% oxygen; the patient is administered a breathing mixture comprising at least 90% oxygen; the breathing mixture includes at least 0.5% $CO_2$; the breathing mixture includes 0.5% to 6% $CO_2$; breathing mixture is administered to the patient at greater than normal atmospheric pressure; the rate of injection is increased until the patient feels a sensation of warmth in a part of the body in need of treatment; the rate of injection is not substantially increased after the patient feels a sensation of warmth; the rate of injection varied to maintain the sensation of warmth for a desired period of time; the total amount of solution administered in one treatment session is between 0.5 ml/kg and 2 ml/kg of patient body weight; the average rate of injection is greater than 0.1 ml/sec; the osmolarity of the solution is less than 1200 mOsm/L; osmolarity of the solution is less than 1100 mOsm/L; the osmolarity of the solution is less than 1000 mOsm/L; the osmolarity of the solution is less than 900 mOsm/L; the osmolarity of the solution is between 200 and 1100 mOsm/L; the solution contains up to 6 mg/ml ascorbic acid; the solution contains 0.1 to 0.7 M (0.1 to 0.6 M, 01 to 0.5 M; 0.15 M to 0.6 M; 0.15 to 0.35 M) magnesium chloride; the solution contains 0.1 to 0.7 M (0.1 to 0.6 M, 01 to 0.5 M; 0.15 M to 0.6 M; 0.15 to 0.35 M)magnesium sulfate; the solution contains 0.1 to 0.7 M (0.1 to 0.6 M, 01 to 0.5 M; 0.15 M to 0.6 M; 0.15 to 0.35 M) $Mg^{2+}$ ions; the patient has suffered a stroke, brain injury, cerebral palsy, viral or chemical injury to the brain; the solution contains one or more of vitamin B12, vitamin B6 and vitamin B5; the solution contains vitamin B12,vitamin B6 and vitamin B5; the solution contains less than 1% by weight calcium gluconate; the solution does not contain calcium gluconate; the solution contain less than 0.001 M $Ca^{2+}$; the breathing mixture is administered through a masking covering the patient's nose and mouth, which masked is sealed to substantially prevent leakage of the breathing mixture; the patient is reclining during treatment; the patient has consumed at least 200 calories within 3 hours prior to treatment; and the patient consumed or has been administered at least 2 ml/kg body weight of water within 3 hours prior to treatment.

BRIEF DESCRIPTION OF THE INVENTION

The methods of the invention, which entail administration of a healing solution containing magnesium ions and additional optional components, can promote more rapid healing of brain injury or other physical trauma than can be achieved without treatment or with only physical therapy. The healing solution administered in the method of the invention has a relatively high level of magnesium ions, at least compared to many commonly used intravenous solutions, and is formulated so as permit the healing solution to be safely and comfortably administered to the patient intravenously at a relatively rapid rate. Thus, the osmolarity and the pH of the solution are set relatively close to physiological levels found in blood.

The healing solution can contain a variety of components in addition to magnesium ions. For example it can contain vitamin C. In some cases, bicarbonate or some other base or a buffer is require to reduce the acidity of solutions containing vitamin C. The healing solution can contain calcium gluconate, but in many cases it is desirable to reduce or eliminate calcium gluconate, particularly where it is desirable to increase the vasodilatory effect of the solution. The healing solution can contain various vitamins, particularly B vitamins, and micronutrients. The healing solution can also include a buffer even where vitamin C is not present.

The healing solution should be injected directly into a vein and should be administered while the patient is breathing a gas mixture that is enriched in oxygen compared to normal air, for example a gas mixture that is greater than 25% (30%, 40%, 50%, 60%, 70%, 80%, 90%) oxygen. In many cases it is desirable to have the patient breath 99-100% oxygen, preferably through a close fitting mask covering the mouth and nose (and preferably sealed to prevent leakage using tape or some other sealant) or through an endotracheal tube. The gas mixture or oxygen is preferably administered at greater than atmospheric pressure, e.g., at a high flow rate or via a pressure bag. Alternatively, the healing solution can be administered to the patient while the patient is in a hyperbaric chamber and breathing a mixture of gasses having at least 25% (30%, 40%, 50%, 60%, 70%, 80%, 90%, 100%) oxygen.

DETAILED DESCRIPTION OF THE INVENTION

The following solutions are useful for preparing the healing solution. All percentages are weight percentages.

| | |
|---|---|
| Sterile Water | |
| Calcium Gluconate 10% | (100 mg/ml) |
| Ascorbic Acid 50% | (500 mg/ml) |
| Magnesium Chloride Hexahydrate 20% | (200 mg/ml) |
| (or Magnesium Sulfate Heptahydrate 50%) | (500 mg/ml) |
| Sodium Bicarbonate 8.4% | (1 mEq/ml) |
| Pyridoxine Hydrochloride (Vitamin B6) 10% | (100 mg/ml) |
| Hydroxocobalamin (Vitamin B12) 1000 mcg/ml | (or 1 mg/ml) |
| Dexpanthenol (Vitamin B5) 25% | (250 mg/ml) |
| Vitamin B-Complex 100 for injection each 1 ml contains: | |
| Thiamin HCl | 100 mg |
| Riboflavin 5' Phosphate Sodium | 2 mg |
| Pyridoxine HCl | 2 mg |
| Dexapanthenol | 2 mg |
| Niacinamide | 100 mg |

To obtain a 60 ml dose of healing solution, the following solution is prepared:

| | |
|---|---|
| Calcium Gluconate (10%) | 1 ml |
| Ascorbic Acid (50%) | 3 ml |
| Magnesium Chloride Hexahydrate (20%) | 8 ml |
| Sodium Bicarbonate (8.4%) | 2 ml |
| Pyridoxine Hydrochloride (10%) | 2 ml |
| Hydroxocobalamin (1 mg/ml) | 2 ml |
| Dexpanthenol (25%) | 2 ml |
| Vitamin B-Complex 100 Injection | 2 ml |
| Sterile water | enough to make a total volume of 60 ml |

The osmolarity of this solution should be about 909 mOsm/L. This osmolarity is higher than the physiological osmolarity of blood, which is about 300mOsm/L, but is lower than commonly used intravenous solutions. It can be desirable to prepare the solution within a few minutes or hours before administration.

The total daily dosage of the healing solution can depend on the age and physical condition of the patient. However, in many cases a dosage of 0.5-2.0 ml/kg of body weight (preferably 0.7 to 1.2 ml/kg body weight, or 0.9 to 1.1 ml/kg body weight is desirable. In some cases it can be desirable to administer the healing solution twice in 24 hour period. In some cases, it is desirable to administer the healing solution several times over a few days.

Before the administration of the healing solution, the administrator must determine the extent of the patient's hydration and nourishment condition. It is desirable for the patient to be adequately hydrated and nourished at the time of the treatment. If the patient has not eaten and is not adequately hydrated within a few hours, e.g., three hours of the treatment the patient might become hypoglycemic, hypotensive, faint or nauseous. If the patient is not thirsty or hungry immediately before being treated he/she should be given between 3-6 ml of water per kg of body weight or a 2.5-9 ml per kg bodyweight intravenously administered saline solution and other nourishment. If the patient is thirsty the hydration amount noted above should be doubled. It is to be noted that the lack of adequate hydration can cause a drop in blood pressure and pain at the site of injection. These factors can limit the operator's ability to administer the solution more rapidly if needed. Adequate hydration generally entails consumption of about 1 ounce of water (or equivalent) per kg of bodyweight in 24 hrs. Adequate nutrition can be defined as at least 100 calories of food consisting of at least 2 of the three groups (carbohydrate, preferably complex carbohydrate, protein, fat).

It is preferable that the patient be reclining during the course of the treatment so as to equalize the natural distribution of the blood supply. Generally, it is preferable the patient be lying flat although the patient can also be sitting or sitting with their legs extended in front.

To administer oxygen, a very close fitting, preferably sealed mask can be used to deliver oxygen, preferably 100% oxygen, or an oxygen-enriched breathing mixture. The oxygen or oxygen-enriched breathing mixture can be administered at greater than atmospheric pressure.

A typical treatment proceeds as follows. Healing solution is injected into a major vein is recommended (a smaller vain can be used but is sometimes less comfortable). Before or upon the start of the administration of the healing solution the oxygen is provided to the patient and is administered to the patient during the entire time that the healing solution is being administered. The patient should feel a sensation of warmth somewhere in the body which may or may not be related to the area of injury. The sensation of warmth may arise from the dilation of blood vessels. In order for the healing solution to have a substantial therapeutic effect, the heat is preferably felt in the area of injury that is being addressed or treated at that session. It is possible that different areas experience heat in sequence because these are all areas that have some form of injury. Indeed, it is often observed that heat is felt in an area of an old injury that has been forgotten by the patient until the area feels warm and then the patient will often remember that he or she had an injury there. Sometimes warmth is felt in immune organs such as thymus area, glands in the neck etc, especially if there is a history of infection that involved these areas.

The healing solution is administered at least until the patient experiences warmth in the area to be treated. If warmth is not felt in the target area, the rate of injection is increased. However, the rate of administration should not be such that there is an adverse change of vital signs, dizziness, light headedness, shortness of breath, chest discomfort or other unexpected uncomfortable sensations. If adverse effects occur, the rate of administration is slowed to that which generates a sensation of warmth in the target area with unreasonable adverse effects. Once warmth is felt in the target area, the rate of administration of the healing solution can be halted or can be maintained at a rate that sustains the sensation of warmth in the target area for a period of time, for example, until the entire dose of healing solution has been administered. The healing solution is administered in an amount and at a rate that allows the sensation of warmth in the targeted are to be maintained for several seconds to several minutes. After the healing solution has been administered, the patient preferably continues to breathe pure oxygen or an oxygen enriched gas mixture for at least one more minute (e.g., at least 5 minutes, at least 10 minutes, at least 20 minutes, or at least 30 minutes). Importantly, feedback from the patient is used to adjust the rate of administration of the solution in order to achieve and maintain the sensation of warmth in the target area to be treated. In some cases it might be possible to use a temperature measuring device to detect and monitor increased warmth in a target region of the patient's body.

EXAMPLE 1

A suitable solution can be made by combining the following components and then adjusting the total volume of solution to 60 ml with sterile water. The osmolarity of this solution is about 813 mOsm/L.

| | |
|---|---|
| Calcium Gluconate 10%: | 1 ml |
| Ascorbic Acid 50% | 3 ml |
| Magnesium Sulfate Heptahydrate 50% | 4 ml |
| Sodium Bicarbonate 8.4% | 3 ml |
| Pyridoxine Hydrochloride (Vitamin B6) 10% | 2 ml |
| Methylcobalamin (Vitamin B12) 1,000 mcg/ml | 2 ml |
| Dexpanthenol (Vitamin B5) 25% | 2 ml |
| Vitamin B-Complex 100 Injection | 2 ml |

EXAMPLE 2

A suitable solution can be made by combining the following components and then adjusting the total volume of solution to 60 ml with sterile water. The osmolarity of this solution is about 820 mOsm.

| | |
|---|---|
| Calcium Gluconate 10% | 1 ml |
| Ascorbic Acid 50% | 3 ml |
| Magnesium Sulfate Heptahydrate 50% | 4 ml |
| Sodium Bicarbonate 8.4% | 3 ml |
| Pyridoxine Hydrochloride (Vitamin B6) 10% | 2 ml |
| Hydroxocobalamin (Vitamin B12) 1,000 mcg/ml | 2 ml |
| Dexpanthenol (Vitamin B5) 25% | 2 ml |
| Vitamin B-Complex 100 Injection | 2 ml |

EXAMPLE 3

A suitable solution can be made by combining the following components and then adjusting the total volume of solution to 60 ml with sterile water. The osmolarity of this solution is about 1041 mOsm.

| | |
|---|---|
| Calcium Gluconate 10% | 1 ml |
| Ascorbic Acid 50% | 3 ml |
| Magnesium Chloride Hexahydrate 20% | 10 ml |
| Sodium Bicarbonate 8.4% | 3 ml |
| Pyridoxine Hydrochloride (Vitamin B6) 10% | 2 ml |
| Hydroxocobalamin (Vitamin B12) 1,000 mcg/ml | 2 ml |
| Dexpanthenol (Vitamin B5) 25% | 2 ml |
| Vitamin B-Complex 100 Injection | 2 ml |

EXAMPLE 4

A suitable solution can be made by combining the following components and then adjusting the total volume of solution to 60 ml with sterile water. The osmolarity of this solution is about 942 mOsm.

| | |
|---|---|
| Calcium Gluconate 10% | 1 ml |
| Ascorbic Acid 50% | 3 ml |

-continued

| | |
|---|---|
| Magnesium Chloride Hexahydrate 20% | 8 ml |
| Sodium Bicarbonate 8.4% | 3 ml |
| Pyridoxine Hydrochloride (Vitamin B6) 10% | 2 ml |
| Hydroxocobalamin (Vitamin B12) 1000 mcg/ml | 2 ml |
| Dexpanthenol (Vitamin B5) 25% | 2 ml |
| Vitamin B-Complex 100 Injection | 2 ml |

What is claimed is:

1. A method for treating a human patient comprising: (a) injecting into the bloodstream of a patient who is breathing a gas mixture having greater than 25% oxygen an aqueous solution comprising: 0.1 to 0.8 M $Mg^{++}$ and having an osmolarity less than 1500 mOSm/l; and (b) increasing the rate of injection at least until the patient feels a sensation of warmth in a target area of the patient's body, wherein the patient has suffered a stroke or brain injury.

2. The method of claim 1 wherein the patient is administered a breathing mixture comprising at least 40% oxygen.

3. The method of claim 2 wherein the patient is administered a breathing mixture comprising at least 60% oxygen.

4. The method of claim 2 wherein the patient is administered a breathing mixture comprising at least 90% oxygen.

5. The method of claim 1 wherein the breathing mixture includes at least 0.5% CO2.

6. The method of claim 1 wherein the breathing mixture includes 0.5% to 6% CO2.

7. The method of claim 2 wherein the breathing mixture is administered to the patient at greater than normal atmospheric pressure.

8. The method of claim 1 wherein the rate of injection is not substantially increased after the patient feels a sensation of warmth.

9. The method of claim 1 wherein the total amount of solution administered is between 0.5 ml/kg and 2 ml/kg of patient body weight.

10. The method of claim 1 wherein the average rate of injection is greater than 0.1 ml/sec.

11. The method of claim 1 wherein the osmolarity of the solution is less than 1200 mOsm/L.

12. The method of claim 1 wherein the osmolarity of the solution is less than 1100 mOsm/L.

13. The method of claim 1 wherein the osmolarity of the solution is less than 1000 mOsm/L.

14. The method of claim 1 wherein the osmolarity of the solution is less than 900 mOsm/L.

15. The method of claim 1 wherein the osmolarity of the solution is between 200 and 1100 mOsm/L.

16. The method of claim 1 wherein the solution contains up to 6 mg/ml ascorbic acid.

17. The method of claim 1 wherein the solution contains 0.1 to 0.7 M magnesium chloride.

18. The method of claim 1 wherein the solution contains 0.1 to 0.7 M magnesium sulfate.

19. The method of claim 1 wherein the solution contains one or more of vitamin B12, vitamin B6 and vitamin B5.

20. The method of claim 1 wherein the solution contains vitamin B12, vitamin B6 and vitamin B5.

21. The method of claim 1 wherein the solution contains less than 1% by weight calcium gluconate.

22. The method claim 1 wherein the solution does not contain calcium gluconate.

23. The method of claim 1 wherein the solution contain less than 0.001 M $Ca^{2+}$.

24. The method of claim 1 wherein the patient is reclining during treatment.

25. The method of claim 1 wherein the patient has consumed at least 200 calories within 3 hours prior to treatment.

26. The method of claim 1 wherein the patient consumed or has been administered at least 2 ml/kg body weight of water within 3 hours prior to treatment.

27. A method of treating a human patient, comprising the steps of:
   a) providing an injectable solution comprising one or more components, including magnesium ions;
   b) administering the solution by injecting the solution into the patient's bloodstream, while adjusting the injection rate based upon temperature feedback from the patient;
   c) providing breathable oxygen comprising at least 25% oxygen, to the patient in the course of administering the solution;
   whereby the solution is administered to the patient at an increasing rate until the patient temperature feedback indicates an increase in warmth in the injured region of the patient, whereupon the injection rate is adjusted in order to maintain the increase in warmth for a desired period of time, wherein the patient has suffered a stroke or brain injury.

28. A method according to claim 27 wherein oxygen is delivered before, during or after administration of the solution.

29. A method according to claim 27 wherein the increase in warmth is maintained for on the order of seconds to minutes.

30. The method of claim 27 wherein the solution contains one or more B vitamins.

* * * * *